(12) United States Patent
Kokeguchi et al.

(10) Patent No.: US 7,766,978 B2
(45) Date of Patent: Aug. 3, 2010

(54) ACIDIC HAIR DYEING METHOD

(75) Inventors: Yuki Kokeguchi, Chiba (JP); Kyoichi Takeda, Chiba (JP); Kiyotaka Kawai, Chiba (JP)

(73) Assignee: Kokyu Alcohol Kogyo Co., Ltd., Chiba (JP)

( * ) Notice: Subject to any disclaimer, the term of this patent is extended or adjusted under 35 U.S.C. 154(b) by 0 days.

(21) Appl. No.: 12/251,537

(22) Filed: Oct. 15, 2008

(65) Prior Publication Data

US 2009/0100609 A1     Apr. 23, 2009

Related U.S. Application Data

(60) Provisional application No. 60/999,489, filed on Oct. 18, 2007.

(51) Int. Cl.
*A61Q 5/08* (2006.01)
*A61Q 5/00* (2006.01)
*C07C 69/66* (2006.01)

(52) U.S. Cl. .................. 8/405; 8/404; 560/176

(58) Field of Classification Search ............ 8/405, 8/404; 560/176
See application file for complete search history.

(56) References Cited

U.S. PATENT DOCUMENTS 2,542,785 A * 2/1951 Walker ............ 252/79
5,601,620 A   2/1997 Ishikawa

FOREIGN PATENT DOCUMENTS

| GB | 1038254 | * | 8/1966 |
|----|---------|---|--------|
| JP | 61036382 | * | 2/1986 |
| JP | 5-105615 |   | 4/1993 |
| JP | 8-225435 |   | 9/1996 |
| JP | 2001-226235 |   | 8/2001 |
| JP | 2002-047150 |   | 2/2002 |
| JP | 2002-104942 |   | 4/2002 |
| JP | 2003-160452 |   | 6/2003 |
| JP | 2004-091427 |   | 3/2004 |
| JP | 2004091427 A | * | 3/2004 |
| JP | 2008-201737 |   | 9/2008 |
| JP | 2009-035497 |   | 2/2009 |

OTHER PUBLICATIONS

CAS Registry No. 10494-02-7 formula structure, accessed in STN on Aug. 13, 2009, available in the STN Registry database since Nov. 16, 1984.*
English abstract of JP 61036382, Derwent Acc. No. 1986-090863.*
Copending U.S. Appl. No. 12/069,119 to Takeda et al.*
Machine translation of Sugimoto, JP 2004091427 A, accessed on the AIPN website on Mar. 3, 2010.*
Abstract of Sugimoto, JP 2004091427 A, accessed from the JPO database.*

* cited by examiner

*Primary Examiner*—Harold Y Pyon
*Assistant Examiner*—Katie Hammer
(74) *Attorney, Agent, or Firm*—Wolf, Greenfield & Sacks, P.C.

(57) ABSTRACT

Provided are acidic hair dye compositions in which the dye has a high permeability into hair, the dye can be applied uniformly, and the composition has excellent staining property, safety and sense of use at the time of hair dyeing. The acidic hair dye compositions of the present invention comprise at least one dibasic acid ester compound represented by general formula I below:

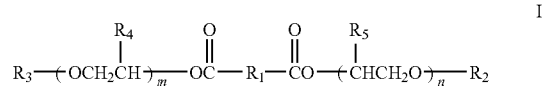

wherein, in general formula I, $R_1$ is an alkylene group which may have a substituent with 2 to 4 carbon atoms, $R_2$ and $R_3$ are, independently from each other, an alkyl group which may have a substituent with 1 to 4 carbon atoms, $R_4$ and $R_5$ are, independently from each other, hydrogen, methyl group or ethyl group, m and n is, independently from each other, an integer of 0 to 4, wherein $m+n \geq 1$ (with the proviso that the case is excluded in which $R_2$ and $R_3$ are both ethyl group, and m and n are both 1).

9 Claims, No Drawings

ACIDIC HAIR DYEING METHOD

RELATED APPLICATION

This application claims the benefit under 35 U.S.C. §119 (e) of U.S. provisional application Ser. No. 60/999,489 filed on Oct. 18, 2007, the entire disclosure of which is incorporated herein by reference.

FIELD OF THE INVENTION

The present invention relates to an acidic hair dye composition with excellent staining property, fastness, texture, safety and sense of use at the time of hair dyeing.

BACKGROUND OF THE INVENTION

Heretofore, as to hair dye compositions, oxidation type hair dyes in which hair dyeing is carried out utilizing an oxidation-reduction reaction, and acidic hair dyes in which hair dyeing is carried out in the acidic condition, are known. Among these, the acidic hair dyes belong to semipermanent hair dyes, and the semipermanent hair dye is a hair dye composition in which hair is dyed by permeating the acidic dye into hair directly.

However, in the previous acidic hair dyes, aromatic alcohols such as benzyl alcohol are exclusively used as a penetration accelerator of the dye (JP, A, 5-105,615, JP, A, 8-225,435 and JP, A, 2002-104,942), and though aromatic alcohols have an action of accelerating penetration of dye into hair, they have a low water solubility, and have the problems on use such as odor at the time of hair dyeing, dripping down when applying to hair to foul cloth, and the problem of safety by irritation to skin, so that no sufficiently satisfactory hair dye has been obtained.

SUMMARY OF THE INVENTION

Therefore, it is the object of the invention to provide an acidic hair dye composition in which the dye has a high permeability into hair, the dye can be applied uniformly, and the composition has excellent staining property, fastness, texture, safety and sense of use at the time of hair dyeing.

From the viewpoint of the above object, the present inventors have researched intensively, and have found that the predetermined ester compounds of dibasic acids have extremely excellent properties as a hair dye, for example, the hair dye has high permeability into hair and good safety, the odor thereof is in the barely-troublesome degree, and led to completion of the present invention by studying such ester compounds of dibasic acids as permeation accelerators of the acidic hair dye.

That is, the present invention relates to an acidic hair dye composition, comprising at least one dibasic acid ester compound represented by general formula I below:

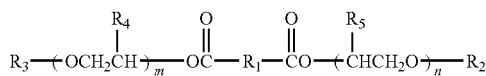

I wherein, in general formula I, $R_1$ is an alkylene group which may have a substituent with 2 to 4 carbon atoms, $R_2$ and $R_3$ are, independently from each other, an alkyl group which may have a substituent with 1 to 4 carbon atoms, $R_4$ and $R_5$ are, independently from each other, hydrogen, methyl group or ethyl group, m and n is, independently from each other, an integer of 0 to 4, wherein m+n≧1 (with the proviso that the case is excluded in which $R_2$ and $R_3$ are both ethyl group, and m and n are both 1).

Also, the present invention relates to the above acidic hair dye composition, wherein, in the above general formula I, one or two types of poly (or mono) ethylene glycol monoethers or derivative components thereof constituting the dibasic acid ester compound are selected from the group consisting of diethylene glycol monoethyl ether, triethylene glycol monoethyl ether, diethylene glycol monopropyl ether, triethylene glycol monopropyl ether, diethylene glycol monoisopropyl ether, triethylene glycol monoisopropyl ether, diethylene glycol monoisobutyl ether, triethylene glycol monoisobutyl ether, propylene glycol monomethyl ether, propylene glycol monoethyl ether, propylene glycol monopropyl ether, propylene glycol monoisopropyl ether, propylene glycol monobutyl ether, propylene glycol monoisobutyl ether, dipropylene glycol monomethyl ether, dipropylene glycol monoethyl ether, dipropylene glycol monopropyl ether, dipropylene glycol monoisopropyl ether, dipropylene glycol monobutyl ether, dipropylene glycol monoisobutyl ether, tripropylene glycol monomethyl ether, tripropylene glycol monoethyl ether, tripropylene glycol monopropyl ether, tripropylene glycol monoisopropyl ether, tripropylene glycol monobutyl ether, tripropylene glycol monoisobutyl ether, tetrapropylene glycol monomethyl ether, tetrapropylene glycol monoethyl ether, tetrapropylene glycol monopropyl ether, tetrapropylene glycol monoisopropyl ether, tetrapropylene glycol monobutyl ether, tetrapropylene glycol monoisobutyl ether, butylene glycol monomethyl ether, butylene glycol monoethyl ether, butylene glycol monopropyl ether, butylene glycol monoisopropyl ether, butylene glycol monobutyl ether, butylene glycol monoisobutyl ether, dibutylene glycol monomethyl ether, dibutylene glycol monoethyl ether, dibutylene glycol monopropyl ether, dibutylene glycol monoisopropyl ether, dibutylene glycol monobutyl ether, dibutylene glycol monoisobutyl ether, tributylene glycol monomethyl ether, tributylene glycol monoethyl ether, tributylene glycol monopropyl ether, tributylene glycol monoisopropyl ether, tributylene glycol monobutyl ether, tributylene glycol monoisobutyl ether, tetrabutylene glycol monomethyl ether, tetrabutylene glycol monoethyl ether, tetrabutylene glycol monopropyl ether, tetrabutylene glycol monoisopropyl ether, tetrabutylene glycol monobutyl ether, and tetrabutylene glycol monoisobutyl ether.

Further, the present invention relates to the above acidic hair dye composition, wherein the dibasic acid is malic acid, succinic acid, tartaric acid or adipic acid.

Also, the present invention relates to the above acidic hair dye composition, wherein the acidic hair dye composition comprises 1.0 to 20.0% by mass of the dibasic acid ester compound based on the total mass of the acidic hair dye composition.

Further, the present invention relates to the above acidic hair dye composition, wherein the acidic hair dye composition further comprises at least one selected from the group consisting of methyl cellulose, ethyl cellulose, hydroxyethyl cellulose (HEC), hydroxyethyl methyl cellulose (HEMC), hydroxypropyl cellulose (HPC), hydroxypropyl methyl cellulose (HPMC), carboxymethyl cellulose (CMC), xanthan gum, carbomer, (acryloyl dimethyltaurine ammonium/VP) copolymer, and (behenel acryloyl dimethyltaurine ammonium methacrylate-25) cross polymer.

Also, the present invention relates to the above acidic hair dye composition, wherein the acidic hair dye composition is adjusted to pH 1.5 to 5.5.

Further, the present invention relates to the above acidic hair dye composition, wherein the acidic hair dye composition comprises 0.001 to 5.0% of an acidic dye based on the total mass of the acidic hair dye composition.

DETAILED DESCRIPTION OF THE INVENTION

According to the present invention, because a dibasic acid ester compound represented by the above general formula I is used as a permeation accelerator, the composition has excellent water solubility, and formulating and designing of the acidic hair dye is easy. In addition, the ester compounds used in the present invention do not have the specific odor of aromatic alcohol that are used as conventional permeation accelerators, and have excellent staining property, particularly excellent texture and safety.

BEST MODE FOR CARRYING OUT THE INVENTION

[I] Acidic Hair Dye Composition (1) Permeation Accelerator

The permeation accelerator used in the acidic hair dye composition of the present invention consists of an ester compound of a dibasic acid represented by general formula I below.

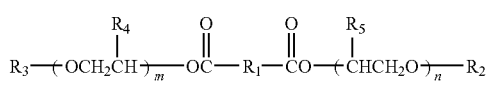

In general formula I, $R_1$ is an alkylene group which may have a substituent with 2 to 4 carbon atoms, $R_2$ and $R_3$ are, independently from each other, an alkyl group which may have a substituent with 1 to 4 carbon atoms, $R_4$ and $R_5$ are, independently from each other, hydrogen, methyl group or ethyl group, m and n is, independently from each other, an integer of 0 to 4, wherein $m+n \geqq 1$ (with the proviso that the case is excluded in which $R_2$ and $R_3$ are both ethyl group, and m and n are both 1).

As to specific examples of $R_1$, ethylene, propylene, isopropylene, butylene, isobutylene etc. are exemplified, and as to the substituents bonded to these alkylene groups, hydroxyl group, alkoxy group, substituted or unsubstituted amino group, ester group etc. are exemplified.

As to specific examples of $R_2$ and $R_3$, methyl, ethyl, n-propyl, isopropyl, n-butyl, isobutyl, sec-butyl, tert-butyl group etc. are exemplified respectively, preferably, methyl, ethyl, n-propyl, isopropyl, butyl, isobutyl group etc., respectively. As to the substituents bonded to these alkyl groups, hydroxyl group, alkoxy group, substituted or unsubstituted amino group, ester group etc. are exemplified. The alkyl group represented by $R_2$ and $R_3$ may be the same or different from each other.

In general formula I above, the poly (or mono) ethylene glycol monoethers or derivative components thereof constituting an ester compound of a dibasic acid, that is, $R_2(OCH_2CHR_5)_nOH$ and $R_3(OCH_2CHR_4)_mOH$, may be respectively the same or different, and as to the preferable specific examples, diethylene glycol monoethyl ether, triethylene glycol monoethyl ether, diethylene glycol monopropyl ether, triethylene glycol monopropyl ether, diethylene glycol monoisopropyl ether, tridiethylene glycol monoisopropyl ether, diethylene glycol monoisobutyl ether, triethylene glycol monoisobutyl ether, propylene glycol monomethyl ether, propylene glycol monoethyl ether, propylene glycol monopropyl ether, propylene glycol monoisopropyl ether, propylene glycol monobutyl ether, propylene glycol monoisobutyl ether, dipropylene glycol monomethyl ether, dipropylene glycol monoethyl ether, dipropylene glycol monopropyl ether, dipropylene glycol monoisopropyl ether, dipropylene glycol monobutyl ether, dipropylene glycol monoisobutyl ether, tripropylene glycol monomethyl ether, tripropylene glycol monoethyl ether, tripropylene glycol monopropyl ether, tripropylene glycol monoisopropyl ether, tripropylene glycol monobutyl ether, tripropylene glycol monoisobutyl ether, tetrapropylene glycol monomethyl ether, tetrapropylene glycol monoethyl ether, tetrapropylene glycol monopropyl ether, tetrapropylene glycol monoisopropyl ether, tetrapropylene glycol monobutyl ether, tetrapropylene glycol monoisobutyl ether, butylene glycol monomethyl ether, butylene glycol monoethyl ether, butylene glycol monopropyl ether, butylene glycol monoisopropyl ether, butylene glycol monobutyl ether, butylene glycol monoisobutyl ether, dibutylene glycol monomethyl ether, dibutylene glycol monoethyl ether, dibutylene glycol monopropyl ether, dibutylene glycol monoisopropyl ether, dibutylene glycol monobutyl ether, dibutylene glycol monoisobutyl ether, tributylene glycol monomethyl ether, tributylene glycol monoethyl ether, tributylene glycol monopropyl ether, tributylene glycol monoisopropyl ether, tributylene glycol monobutyl ether, tributylene glycol monoisobutyl ether, tetrabutylene glycol monomethyl ether, tetrabutylene glycol monoethyl ether, tetrabutylene glycol monopropyl ether, tetrabutylene glycol monoisopropyl ether, tetrabutylene glycol monobutyl ether, tetrabutylene glycol monoisobutyl ether, etc. are exemplified.

In the acidic hair dye composition of the present invention, only one ester compound represented by general formula I may be used, and two or more may be used in combination.

The dibasic acid constituting the ester compound represented by general formula I is a dibasic acid with 2 to 4 carbon atoms, preferably malic acid, succinic acid, tartaric acid or adipic acid.

As to preferable specific examples of ester compounds of dibasic acids in which $R_4$ and $R_5$ are each hydrogen, bisethylene glycol succinate ethyl ether, bisdiethylene glycol succinate ethyl ether (bisethoxy diglycol succinate), bistriethylene glycol succinate ethyl ether, bisethylene glycol succinate propyl ether, bisdiethylene glycol succinate propyl ether, bistriethylene glycol succinate propyl ether, bisethylene glycol succinate isopropyl ether, bisdiethylene glycol succinate isopropyl ether, bistriethylene glycol succinate isopropyl ether, bisethylene glycol succinate isobutyl ether, bisdiethylene glycol succinate isobutyl ether, bistriethylene glycol succinate isobutyl ether, bisethylene glycol malate ethyl ether, bisdiethylene glycol malate ethyl ether, bistriethylene glycol malate ethyl ether, bisethylene glycol malate propyl ether, bisdiethylene glycol malate propyl ether, bistriethylene glycol malate propyl ether, bisethylene glycol malate isopropyl ether, bisdiethylene glycol malate isopropyl ether, bistriethylene glycol malate isopropyl ether, bisethylene glycol malate isobutyl ether, bisdiethylene glycol malate isobutyl ether, bistriethylene glycol malate isobutyl ether, bisethylene glycol tartrate ethyl ether, bisdiethylene glycol tartrate ethyl ether, bistriethylene glycol tartrate ethyl ether, bisethylene glycol tartrate propyl ether, bisdiethylene glycol tartrate propyl ether, bistriethylene glycol tartrate propyl ether, bisethylene glycol tartrate isopropyl ether, bisdiethylene glycol tartrate isopropyl ether, bistriethylene glycol tartrate isopropyl ether, bisethylene glycol tartrate isobutyl ether, bisdiethylene glycol tartrate isobutyl ether, bistriethylene glycol tartrate isobutyl ether, bisethylene glycol adipate ethyl ether, bisdiethylene glycol adipate ethyl ether, bistriethylene glycol adipate ethyl ether, bisethylene glycol adipate propyl ether, bisdiethylene glycol adipate propyl ether, bistriethylene glycol adipate propyl ether, bisglycol adipate isopropyl ether, bisdiethylene glycol adipate isopropyl ether, bistriethylene glycol adipate isopropyl ether, bisethylene glycol adipate isobutyl ether, bisdiethylene glycol adipate isobutyl ether, bistriethylene glycol adipate isobutyl ether etc. are exemplified.

As to preferable specific examples of ester compounds of dibasic acids in which $R_4$ and $R_5$ are each methyl group, bispropylene glycol succinate ethyl ether, bisdipropylene glycol succinate ethyl ether, bistripropylene glycol succinate ethyl ether, bispropylene glycol succinate propyl ether, bisdipropylene glycol succinate propyl ether, bistripropylene glycol succinate propyl ether, bispropylene glycol succinate isopropyl ether, bisdipropylene glycol succinate isopropyl ether, bistripropylene glycol succinate isopropyl ether, bispropylene glycol succinate isobutyl ether, bisdipropylene glycol succinate isobutyl ether, bistripropylene glycol succinate isobutyl ether, bispropylene glycol malate ethyl ether, bisdipropylene glycol malate ethyl ether, bistripropylene glycol malate ethyl ether, bispropylene glycol malate propyl ether, bisdipropylene glycol malate propyl ether, bistripropylene glycol malate propyl ether, bispropylene glycol malate isopropyl ether, bisdipropylene glycol malate isopropyl ether, bistripropylene glycol malate isopropyl ether, bispropylene glycol malate isobutyl ether, bisdipropylene glycol malate isobutyl ether, bistripropylene glycol malate isobutyl ether, bispropylene glycol tartrate ethyl ether, bisdipropylene glycol tartrate ethyl ether, bistripropylene glycol tartrate ethyl ether, bispropylene glycol tartrate propyl ether, bisdipropylene glycol tartrate propyl ether, bistripropylene glycol tartrate propyl ether, bispropylene glycol tartrate isopropyl ether, bisdipropylene glycol tartrate isopropyl ether, bistripropylene glycol tartrate isopropyl ether, bispropylene glycol tartrate isobutyl ether, bisdipropylene glycol tartrate isobutyl ether, bistripropylene glycol tartrate isobutyl ether, bispropylene glycol adipate ethyl ether, bisdipropylene glycol adipate ethyl ether, bistripropylene glycol adipate ethyl ether, bispropylene glycol adipate propyl ether, bisdipropylene glycol adipate propyl ether, bistripropylene glycol adipate propyl ether, bispropylene glycol adipate isopropyl ether, bisdipropylene glycol adipate isopropyl ether, bistripropylene glycol adipate isopropyl ether, bispropylene glycol adipate isobutyl ether, bisdipropylene glycol adipate isobutyl ether, bistripropylene glycol adipate isobutyl ether etc. are exemplified.

As to preferable specific examples of ester compounds of dibasic acids in which $R_4$ and $R_5$ are each ethyl group, bisbutylene glycol succinate ethyl ether, bisdibutylene glycol succinate ethyl ether, bistributylene glycol succinate ethyl ether, bisbutylene glycol succinate propyl ether, bisdibutylene glycol succinate propyl ether, bistributylene glycol succinate propyl ether, bisbutylene glycol succinate isopropyl ether, bisdibutylene glycol succinate isopropyl ether, bistributylene glycol succinate isopropyl ether, bisbutylene glycol succinate isobutyl ether, bisdibutylene glycol succinate isobutyl ether, bistributylene glycol succinate isobutyl ether, bisbutylene glycol malate ethyl ether, bisdibutylene glycol malate ethyl ether, bistributylene glycol malate ethyl ether, bisbutylene glycol malate propyl ether, bisdibutylene glycol malate propyl ether, bistributylene glycol malate propyl ether, bisbutylene glycol malate isopropyl ether, bisdibutylene glycol malate isopropyl ether, bistributylene glycol malate isopropyl ether, bisbutylene glycol malate isobutyl ether, bisdibutylene glycol malate isobutyl ether, bistributylene glycol malate isobutyl ether, bisbutylene glycol tartrate ethyl ether, bisdibutylene glycol tartrate ethyl ether, bistributylene glycol tartrate ethyl ether, bisbutylene glycol tartrate propyl ether, bisdibutylene glycol tartrate propyl ether, bistributylene glycol tartrate propyl ether, bisbutylene glycol tartrate isopropyl ether, bisdibutylene glycol tartrate isopropyl ether, bistributylene glycol tartrate isopropyl ether, bisbutylene glycol tartrate isobutyl ether, bisdibutylene glycol tartrate isobutyl ether, bistributylene glycol tartrate isobutyl ether, bisbutylene glycol adipate ethyl ether, bisdibutylene glycol adipate ethyl ether, bistributylene glycol adipate ethyl ether, bisbutylene glycol adipate propyl ether, bisdibutylene glycol adipate propyl ether, bistributylene glycol adipate propyl ether, bisbutylene glycol adipate isopropyl ether, bisdibutylene glycol adipate isopropyl ether, bistributylene glycol adipate isopropyl ether, bisbutylene glycol adipate isobutyl ether, bisdibutylene glycol adipate isobutyl ether, bistributylene glycol adipate isobutyl ether etc. are exemplified.

The content of the ester compound represented by general formula I is preferably 1 to 20% by mass, more preferably 2 to 15% by mass, based on the total mass of the acidic hair dye composition. If the content of the ester compound is low, a sufficient effect as the permeation accelerator can not be obtained, and staining property is inferior. On the other hand, if the content of the ester compound is too high, the effect of further excellent staining property can not be obtained, so that it is uneconomical.

(2) Acidic Dye

The acidic dye contained in the acidic hair dye composition is not specifically limited, but, for example, Red No. 2 (C.I. 16185), Red No. 3 (C.I. 45430), Red No. 102 (C.I. 16255), Red No. 104 (C.I. 45410), Red No. 105 (C.I. 45440), Red No. 106 (C.I. 45100), Yellow No. 4 (C.I. 19140), Yellow No. 5 (C.I. 15985), Green No. 3 (C.I. 42053), Blue No. 1 (C.I. 42090), Blue No. 2 (C.I. 73015), Red No. 227 (C.I. 17200), Red No. 230 (C.I. 45380), Orange No. 205 (C.I. 15510), Yellow No. 202 (C.I. 45350), Yellow No. 203 (C.I. 47005), Green No. 201 (C.I. 61570), Green No. 204 (C.I. 59040), Blue No. 205 (C.I. 42090), Brown No. 201 (C.I. 20170), Red No. 401 (C.I. 45190), Red No. 504 (C.I. 14700), Orange No. 402 (C.I. 14600), Yellow No. 403 (C.I. 12100), Yellow No. 406 (C.I. 13065), Yellow No. 407 (C.I. 18820), Green No. 401 (C.I. 10020), Purple No. 401 (C.I. 60730), Black No. 401 (C.I. 60730) etc. can be exemplified. One or more of these acidic dyes can be used in order to provide a desired tint.

The content of the acidic dye is preferably in the range of 0.001 to 5% by mass, further 0.01 to 3% by mass is preferable, based on the total mass of the acidic hair dye composition. If the content of the acidic dye is low, staining property can not be sufficiently exerted, and the object of the present invention can not be accomplished. On the other hand, if the content of the acidic dye is too high, further excellent staining property can not be obtained, so that it is uneconomical.

(3) pH

The pH of the acidic hair dye composition of the present invention is preferably 1.5 to 5.5, with 1.6 to 4.5 being more preferable. When the pH of the composition is low, a problem occurs in safety due to skin irritation etc., and when the pH is high, staining property deteriorates. pH regulator may be used in order to adjust pH of the hair dye composition within a preferable range. As to the pH regulators, organic acids, such as citric acid, tartaric acid, acetic acid, lactic acid, glycolic acid, succinic acid, malic acid, fumaric acid, butyric acid, valeric acid, oxalic acid, maleic acid, mandelic acid, adipic acid, etc., inorganic acids, such as phosphoric acid, hydrochloric acid, nitric acid, sulfuric acid, etc., and salts thereof, are exemplified. As to the salts, sodium salt, potassium salt, ammonium salt, alkanolamine salts such as triethanolamine salt, etc. are exemplified. pH regulator is preferably phosphoric acid, acetic acid, lactic acid, glycolic acid or succinic acid. The compounding amount thereof may be determined accordingly from the relation with pH to be regulated.

(4) Water-Soluble Polymers

The acidic hair dye composition of the present invention may contain water-soluble polymers for providing the effect such as thickening property. As to the water-soluble polymers, methyl cellulose, ethyl cellulose, hydroxyethyl cellulose (HEC), hydroxyethyl methyl cellulose (HEMC), hydroxypropyl cellulose (HPC), hydroxypropyl methyl cellulose (HPMC), carboxymethyl cellulose (CMC), xanthan gum, carbomer, (acryloyl dimethyl taurine ammonium/VP) copolymer, (behenel acryloyl dimethyl taurine ammonium methacrylate-25) cross polymer etc. are exemplified. One of these water-soluble polymers may be used, or two or more may be used in combination.

The content of the water-soluble polymers is preferably 0.01 to 10% by mass, with 0.1 to 8% by mass being more preferable, based on the total mass of the acidic hair dye composition. When the compounding amount is too low or too high, the desired stickiness can not be obtained, so that stability deteriorates, and that the hair dye can not be uniformly applied, etc.

(5) Other Ingredients

The acidic hair dye composition of the present invention may contain other ingredients that are usually used in the field of hair dye to the extent that the effect of the present invention is not impaired. As to other ingredients, oily ingredients, alcohols, polyhydric alcohols, etc. are exemplified. Further, anionic surfactants, nonionic surfactants, humectants, botanical extracts, pigments, colorants, antiseptics, chelating agents, antioxidants, UV absorbers, fragrances etc. can also be blended to the extent that pH is not influenced.

As to the oily ingredients, animal oils, vegetable oils, hydrocarbon oils, silicone oils, ester oils, etc. are exemplified, and specifically, isotridecyl isononanoate, polyglyceryl triisostearate, diisostearyl malate, trimethylolpropane triethylhexanoate, neopentyl glycol diethylhexanoate, isostearyl neopentanoate, triisostearin, pentaerythrityl tetraethylhexanoate, pentaerythrityl tetraisostearate, octyldodecyl stearoyloxystearate, neopentyl glycol dicaprate, microcrystalline wax, candelilla wax, ceresin, jojoba seed oil, etc. are exemplified. As to alcohols, lower alcohols such as methanol, ethanol, propyl alcohol, isopropyl alcohol, butanol, etc., higher alcohols such as lauryl alcohol, myristyl alcohol, cetyl alcohol, stearyl alcohol, behenyl alcohol, cetostearyl alcohol, etc. are exemplified. Further, as to polyhydric alcohols, propylene glycol, dipropylene glycol, glycerin, 1,3-butylene glycol, isoprene glycol, diglycerin, maltitol, sorbitol, etc. are exemplified.

[II] Production Process

The acidic hair dye composition of the present invention is usually made to the agent form, such as cream, emulsion, gel, solution, mousse, foam, etc. When gel form acidic hair dye composition is produced, the composition can be produced by, for example, stirring an ester compound represented by general formula I together with alcohols, water-soluble polymers, etc., dispersing uniformly, thereafter adding an acidic dye and a pH regulator, and adjusting to the desired pH. Also, cream or emulsion form acidic hair dye composition can be produced by blending an emulsifier, a solubilizer, a styling spritz etc. usually employed in the field of cosmetics together with the above ingredients. For example, the composition can be produced by stirring ester compounds represented by general formula I, alcohols, polyhydric alcohols, the above oily ingredients such as animal oils and vegetable oils, hair dye ingredients such as water-soluble polymers, pH regulators, acidic dyes, etc. uniformly while heating, emulsifying, thereafter cooling to be cream or emulsion form. Further, as to the acidic hair dye composition of mousse or foam agent form, for example, acidic hair dyes, penetration accelerators, pH regulators, surfactants and thickeners (water-soluble polymers) are dissolved and dispersed, thereafter filled into an aerosol can together with a liquefied petroleum gas (a propellant), and sprayed in mousse or foam form at the time of use.

EXAMPLES

The present invention is described in more detail by way of Examples as follows, however, the present invention is not limited to these Examples.

Examples 1 to 3

Gel Form Acidic Hair Dye Composition

The acidic hair dye composition composed as shown in Table 1 was prepared by the following preparation method, and evaluated by the following evaluation method. The results are shown in Table 1.

[Preparation Method]

Bisethoxy diglycol succinate (or benzyl alcohol), ethanol and hydroxyethyl cellulose (or xanthan gum) were added to purified water, stirred, and dispersed uniformly. Then, to this, Red No. 227 (or Orange No. 205) previously dissolved in purified water was added, and further dispersed uniformly. After confirmed uniform dissolution, lactic acid was added to adjust the pH to 3.5 to 4.0 to obtain a red acidic hair dye composition.

[Evaluation Method]

(1) Odor of Hair Dye

Odor at the time of hair dyeing was evaluated by 10 panelists, and judged according to the following criteria.

◯: The percentage of those who evaluated that there was no unpleasant odor at the time of hair dyeing is 80% or more.

Δ: The percentage of those who evaluated that there was no unpleasant odor at the time of hair dyeing is from 20% or more to less than 80%.

X: The percentage of those who evaluated that there was no unpleasant odor at the time of hair dyeing is less than 20%.

(2) Staining Property 1 g of acidic hair dye composition was applied uniformly on 1 g of yak hair, and allowed to stand at 40° C. for 20 minutes. Then it was washed with water, washed twice with aqueous 10% sodium lauryl sulfate solution, and then dried. The staining property of this hair dye sample was evaluated visually by 10 panelists, and judged according to the following criteria.

◯: The percentage of those who evaluated that the staining property on yak hair is good is 80% or more.

Δ: The percentage of those who evaluated that the staining property on yak hair is good is from 20% or more to less than 80%.

X: The percentage of those who evaluated that the staining property on yak hair is good is less than 20%.

(3) Fastness 1 g of acidic hair dye composition was applied uniformly on 1 g of yak hair, and allowed to stand at 40° C. for 20 minutes. Then it was washed with water, washed twice with aqueous 10% sodium lauryl sulfate solution, and then dried. Further, this yak hair was treated ten times by aqueous 10% sodium lauryl sulfate solution, and dried. The fastness of this hair dye sample was evaluated visually by 10 panelists, and judged according to the following criteria.

◯: The percentage of those who evaluated that the fastness on yak hair is good is 80% or more.

Δ: The percentage of those who evaluated that the fastness on yak hair is good is from 20% or more to less than 80%.

X: The percentage of those who evaluated that the fastness on yak hair is good is less than 20%.

(4) Texture 1 g of acidic hair dye composition was applied uniformly on 1 g of yak hair, and allowed to stand at 40° C. for 20 minutes. Then it was washed with water, washed twice with aqueous 10% sodium lauryl sulfate solution, and then dried. As to this hair dye sample, softness and combing property were evaluated by 10 panelists, and judged according to the following criteria.

◯: The percentage of those who evaluated that the dyed yak hair is soft and easy to comb is 80% or more.

Δ: The percentage of those who evaluated that the dyed yak hair is soft and easy to comb is from 20% or more to less than 80%.

X: The percentage of those who evaluated that the dyed yak hair is soft and easy to comb is less than 20%.

(5) Safety

Ten male and ten female, total 20 subjects were blocked and applied on the skin in the forearm flexor part with 0.05 g of sample using a circular bandaid for patch test provided with lint with 1.0 cm diameter for 2 hours. Thereafter, applied affected part was washed away, and the skin conditions of 20 subjects 24 hours after the bandaid was removed were judged and evaluated according to the following evaluation criteria.

When the evaluation (−) was in 20 subjects, the condition was judged as "◯", when the evaluation (±) was in 1 to 2 subjects, the condition was judged as "Δ", when the evaluation (±) was in 3 or more subjects or the evaluations (+) to (+++) were in one or more subjects, the condition was judged as "X".

(Evaluation Criteria)

(Skin Condition) (Evaluation)

Erythema, edema, blister: (+++)

Erythema, edema: (++)

Erythema: (+)

Slight erythema: (±)

No erythema, no edema: (−)

TABLE 1

| | Ingredients | Example 1 (% by mass) | Example 2 (% by mass) | Example 3 (% by mass) | Comparative example 1 (% by mass) |
|---|---|---|---|---|---|
| A | Bisethoxy diglycol succinate | 3.0 | 5.0 | 10.0 | — |
| | Benzyl alcohol | — | — | — | 5.0 |
| B | Purified water | Rest | Rest | Rest | Rest |
| C | Ethanol | 25.0 | 25.0 | 15.0 | 25.0 |
| D | Lactic acid | 5.0 | 5.0 | — | 5.0 |
| | Glycolic acid | — | — | 2.0 | 5.0 |
| E | Hydroxyethyl cellulose | 2.0 | 2.0 | — | 2.0 |
| | Xanthan gum | — | — | 5.0 | — |
| F | Red No. 227 (C.I. 17200) | 0.2 | 0.5 | — | 0.5 |
| | Orange No. 205 (C.I. 15510) | — | — | 0.8 | — |
| Property evaluations | Odor of hair dye | ◯ | ◯ | ◯ | X |
| | Staining property | ◯ | ◯ | ◯ | ◯ |
| | Fastness | ◯ | ◯ | ◯ | ◯ |
| | Texture | ◯ | ◯ | ◯ | Δ |
| | Safety | ◯ | ◯ | ◯ | Δ |

Comparative Example 1

An acidic hair dye composition was prepared similar to Example 1, except that benzyl alcohol was used instead of bisethoxy diglycol succinate as the permeation accelerator. The acidic hair dye composition obtained was evaluated in a similar way to Example 1. The results are shown in Table 1.

As can be seen from Table 1, the acidic hair dye compositions according to Examples 1 to 3 showed good results as to all of odor of hair dye, staining property, fastness, texture and safety, but the acidic hair dye composition according to Comparative example 1 showed inferior results as to odor of hair dye and safety, and further a slightly inferior result as to texture.

Examples 4 to 7

Gel Form Acidic Hair Dye Composition

Acidic hair dye compositions composed as shown in Table 2 were prepared by a preparation method similar to Examples 1 to 3, and acidic hair dye compositions obtained were evaluated by an evaluation method similar to Examples 1 to 3. The results are shown in Table 2. The acidic hair dye compositions according to Examples 4 to 7 showed good properties as to odor of the hair dye, staining property, fastness, texture and safety.

TABLE 2

|   | Ingredients | Example 4 (% by mass) | Example 5 (% by mass) | Example 6 (% by mass) | Example 7 (% by mass) |
|---|---|---|---|---|---|
| A | Bisethylene glycol succinate isobutyl ether | 4.0 | — | — | — |
|   | Bispropylene glycol malate ethyl ether | — | 5.5 | — | — |
|   | Bisbutylene glycol tartrate ethyl ether | — | — | 3.5 | — |
|   | Bistriethylene glycol adipate isopropyl ether | — | — | — | 2.0 |
| B | Purified water | Rest | Rest | Rest | Rest |
| C | Ethanol | 25.0 | 20.0 | 25.0 | 25.0 |
|   | Dipropylene glycol | — | 5.0 | — | — |
| D | Lactic acid | — | 2.5 | — | — |
|   | Glycolic acid | — | — | — | 2.0 |
|   | Tartaric acid | 3.0 | — | — | — |
|   | Phosphoric acid | — | — | 0.5 | — |
| E | Hydroxyethyl cellulose | 2.0 | — | — | — |
|   | Xanthan gum | — | 4.5 | — | — |
|   | Carboxymethyl cellulose | — | — | 3.3 | — |
|   | (Acryloyl dimethyl taurin ammonium/VP) copolymer | — | — | — | 1.8 |
| F | Yellow No. 4 (C.I. 19140) | — | — | — | 0.01 |
|   | Orange No. 205 (C.I. 15510) | 0.16 | 0.24 | 0.10 | — |
|   | Black No. 401 (C.I. 60730) | 0.06 | 0.14 | 0.20 | 0.02 |
|   | Purple No. 401 (C.I. 60730) | 0.05 | 0.14 | 0.10 | 0.03 |
| Property evaluations | Odor of hair dye | ○ | ○ | ○ | ○ |
|   | Staining property | ○ | ○ | ○ | ○ |
|   | Fastness | ○ | ○ | ○ | ○ |
|   | Texture | ○ | ○ | ○ | ○ |
|   | Safety | ○ | ○ | ○ | ○ |

Example 8

Cream Form Acidic Hair Dye Composition

A cream form acidic hair dye composition composed as shown in Table 3 was prepared by the following preparation method, and evaluated by an evaluation method similar to Examples 1 to 3.

[Preparation Method]

Ingredients (1 to 5, oil phase), ingredients (6 to 12, water phase) were each heated to 75 to 80° C., dissolved uniformly, the oily phase was added to the aqueous phase while stirring, and emulsified by a homomixer. Then, the mixture was gradually cooled to 30° C. while stirring to obtain a cream form acidic hair dye composition.

The cream form acidic hair dye composition obtained showed good properties as to all of odor of hair dye, staining property, fastness, texture, and safety.

TABLE 3

| No. | Ingredients | Compounding amount (% by mass) |
|---|---|---|
| 1 | Cetostearyl alcohol | 2.0 |
| 2 | Behenyl alcohol | 1.0 |
| 3 | Dipropylene glycol | 5.0 |
| 4 | (Polyglyceryl-2 isostearate/dimer dilinoleic acid) copolymer | 2.0 |
| 5 | Polyglyceryl stearate-10 | 1.5 |
| 6 | (Acryloyl dimethyl taurin ammonium/VP) copolymer | 1.7 |
| 7 | Bisethoxy diglycol succinate | 6.0 |
| 8 | Ethanol | 20.0 |
| 9 | Lactic acid | 5.0 |
| 10 | Purified water | Rest |
| 11 | Yellow No. 4 (C.I. 19140) | 0.5 |
| 12 | Black No. 401 (C.I. 60730) | 0.25 |
| Property evaluations | Odor of hair dye | ○ |
|   | Staining property | ○ |
|   | Fastness | ○ |
|   | Texture | ○ |
|   | Safety | ○ |

The invention claimed is:

1. A method for dyeing hair comprising applying to hair an acidic hair dye composition comprising at least one dibasic acid ester compound represented by general formula I below:

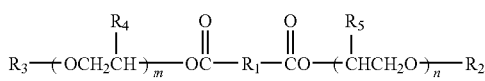

wherein, in general formula I, $R_1$ is an alkylene group with 2 to 4 carbon atoms, $R_2$ and $R_3$ are each independently an alkyl group with 1 to 4 carbon atoms, $R_4$ and $R_5$ are each independently hydrogen, methyl group or ethyl group, m and n are each independently an integer of 0 to 4, wherein $m+n \geq 1$ (with the proviso that the case is excluded in which $R_2$ and $R_3$ are both ethyl group, and m and n are both 1).

2. The method of dyeing hair according to claim 1, wherein, in general formula I according to claim 1, one or two types of poly (or mono) ethylene glycol monoethers or derivative components thereof constituting the dibasic acid ester compound are selected from the group consisting of diethylene glycol monoethyl ether, triethylene glycol monoethyl ether, diethylene glycol monopropyl ether, triethylene glycol monopropyl ether, diethylene glycol monoisopropyl ether, triethylene glycol monoisopropyl ether, diethylene glycol monoisobutyl ether, triethylene glycol monoisobutyl ether, propylene glycol monomethyl ether, propylene glycol monoethyl ether, propylene glycol monopropyl ether, propylene glycol monoisopropyl ether, propylene glycol monobutyl ether, propylene glycol monoisobutyl ether, dipropylene glycol monomethyl ether, dipropylene glycol monoethyl ether, dipropylene glycol monopropyl ether, dipropylene glycol monoisopropyl ether, dipropylene glycol monobutyl ether, dipropylene glycol monoisobutyl ether, tripropylene glycol monomethyl ether, tripropylene glycol monoethyl ether, tripropylene glycol monopropyl ether, tripropylene glycol monoisopropyl ether, tripropylene glycol monobutyl ether, tripropylene glycol monoisobutyl ether, tetrapropylene glycol monomethyl ether, tetrapropylene glycol monoethyl ether, tetrapropylene glycol monopropyl ether, tetrapropylene glycol monoisopropyl ether, tetrapropylene glycol monobutyl ether, tetrapropylene glycol monoisobutyl ether, butylene glycol monomethyl ether, butylene glycol monoethyl ether, butylene glycol monopropyl ether, butylene glycol monoisopropyl ether, butylene glycol monobutyl ether, butylene glycol monoisobutyl ether, dibutylene glycol monomethyl ether, dibutylene glycol monoethyl ether, dibutylene glycol monopropyl ether, dibutylene glycol monoisopropyl ether, dibutylene glycol monobutyl ether, dibutylene glycol monoisobutyl ether, tributylene glycol monomethyl ether, tributylene glycol monoethyl ether, tributylene glycol monopropyl ether, tributylene glycol monoisopropyl ether, tributylene glycol monobutyl ether, tributylene glycol monoisobutyl ether, tetrabutylene glycol monomethyl ether, tetrabutylene glycol monoethyl ether, tetrabutylene glycol monopropyl ether, tetrabutylene glycol monoisopropyl ether, tetrabutylene glycol monobutyl ether, and tetrabutylene glycol monoisobutyl ether.

3. The method of dyeing hair according to claim 1, wherein the dibasic acid is malic acid, succinic acid, tartaric acid or adipic acid.

4. The method of dyeing hair according to claim 1, wherein the acidic hair dye composition comprises 1 to 20% by mass of the dibasic acid ester compound based on the total mass of the acidic hair dye composition.

5. The method of dyeing hair according to claim 1, wherein the acidic hair dye composition further comprises at least one compound selected from the group consisting of methyl cellulose, ethyl cellulose, hydroxyethyl cellulose (HEC), hydroxyethyl methyl cellulose (HEMC), hydroxypropyl cellulose (HPC), hydroxypropyl methyl cellulose (HPMC), carboxymethyl cellulose (CMC), xanthan gum, carbomer, (acryloyl dimethyl taurine ammonium/VP) copolymer, and (behenel acryloyl dimethyl taurine ammonium methacrylate-25) cross polymer.

6. The method of dyeing hair according to claim 1, wherein the acidic hair dye composition is adjusted to pH 1.5 to 5.5.

7. The method of dyeing hair according to claim 1, wherein the acidic hair dye composition comprises 0.001 to 5% by mass of an acidic dye based on the total mass of the acidic hair dye composition.

8. A method for dyeing hair according to claim 1, where $R_1$ of general formula I has a substituent.

9. A method for dyeing hair according to claim 1, where $R_2$ and/or $R_3$ of general formula I have a substituent.

* * * * *